(12) United States Patent
Malowaniec

(10) Patent No.: US 6,402,730 B1
(45) Date of Patent: Jun. 11, 2002

(54) LIQUID IMPERMEABLE DISPOSABLE HYGIENIC ARTICLE FOR ONE TIME USE WITH AN IMPROVED FASTENING SYSTEM

(75) Inventor: Krzysztof D. Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 09/446,136

(22) PCT Filed: Jun. 10, 1998

(86) PCT No.: PCT/EP98/03512

§ 371 (c)(1),
(2), (4) Date: Dec. 30, 1999

(87) PCT Pub. No.: WO99/01100

PCT Pub. Date: Jan. 14, 1999

(30) Foreign Application Priority Data

Jul. 1, 1997 (DE) .......................................... 197 27 916

(51) Int. Cl.⁷ .................................................. A61F 13/58
(52) U.S. Cl. ....................................... 604/389; 604/391
(58) Field of Search ................................... 604/389, 391

(56) References Cited

U.S. PATENT DOCUMENTS 5,611,791 A    3/1997   Gorman et al.

FOREIGN PATENT DOCUMENTS

| EP | 0247855 A2 | 12/1987 |
| EP | 0324577 A1 | 7/1989 |
| EP | 0719532 A1 | 7/1996 |
| WO | WO 96/25905 | 8/1996 |

*Primary Examiner*—John J. Calvert
*Assistant Examiner*—Angela J. Grayson
(74) *Attorney, Agent, or Firm*—Jones, Tullar & Cooper, P.C.

(57) ABSTRACT

A disposable hygienic article, in particular a diaper, an incontinence product or incontinence insert, has a fastening system for detachably linking a rear region and a front region of the hygienic article placed on the user and for fixing the used article in the rolled-up or folded state before it is thrown away or disposed of The fastening system has a first fastening section with retaining means in the rear region and a second fastening section with matching retaining means in the front region. The first fastening section can be positioned on the second fastening section when the rear region and front region are linked, to allow the retaining means and matching retaining means to be mechanically joined. The rataining means of the first fastening section are adhesive.

40 Claims, 4 Drawing Sheets

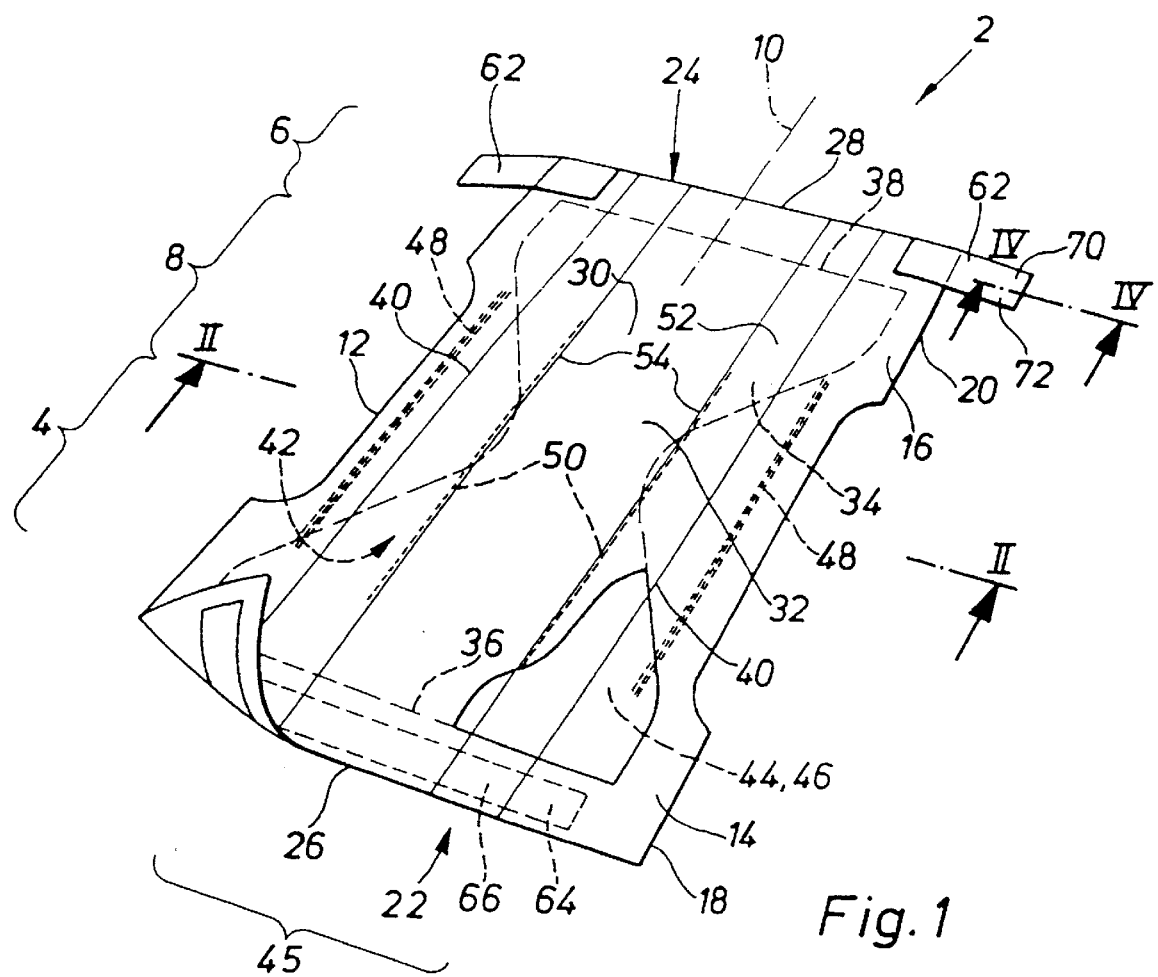
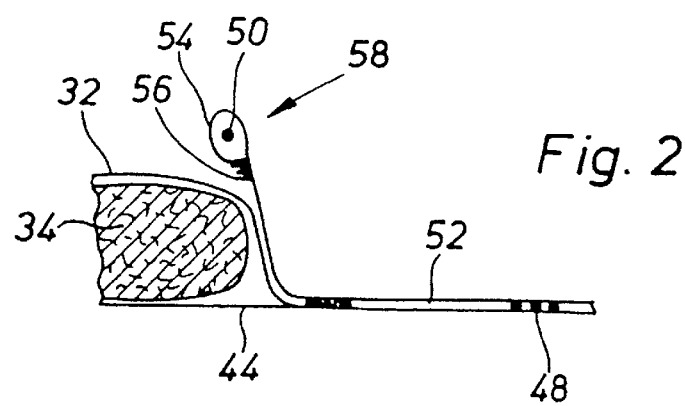

US 6,402,730 B1

LIQUID IMPERMEABLE DISPOSABLE HYGIENIC ARTICLE FOR ONE TIME USE WITH AN IMPROVED FASTENING SYSTEM

FIELD OF THE INVENTION

The invention present relates to an hygienic article for one-time use, in particular a diaper, an incontinence product or an incontinence liner, having a front area, a rear area and a center area located between them, which comes to lie in the crotch area of the user of the hygienic article, the hygienic article has a layer, which constitutes the outside facing away from the body and is inpermeable to liquid at least in parts of it, and a layer, which constitutes the inside facing. It also has body and is liquid-permeable at least in the area of an absorbent body arranged under it, a fastening system for the releasable connection of the rear and front areas of the hygienic article when it is placed on the body of the user and for securing the used article when it is rolled up or folded together for being thrown away or disposed of, wherein the fastening system has a first fastening section with securing means at the rear area, and a second fastening section with counter-securing means at the front area so that, the rear area and the front area are connected, the first securing section can be positioned on the second fastening section so that the securing means and counter-securing means can enter into a mechanical securing connection, the securing means of the first fastening section in addition.

BACKGROUND OF THE INVENTION

For putting on such an hygienic article, which absorbs body fluids and bodily excretions, the rear area and the front area are placed against the body of the user, wherein the lateral edges of the rear area and the front area are at least approximately adjoining or overlap each other so that, using the fastening system, the front and rear areas can be connected in an as optimal as possible fit of the article on the body of the user, so that an escape of body fluids or bodily excretions is prevented, helped by further aids, such as resilienty stretchable liquid barriers, bands and the suitable dimensioning of the absorbent body. For exchanging the used hygienic article for a fresh one, the fastening system is released, and the hygienic article containing body fluids and bodily excretions is taken off the user. In order to make the used hygienic article easier to dispose of, it is customarily rolled up or folded from the front area in the direction towards the rear area, so that a small package is formed, which can be manipulated and which the user, the parents or a caretaker, can pick up manually and throw into a disposal container. In order to furthermore prevent the rolled or folded up small package from opening again when it is thrown away, or thereafter in the disposal container, which leads to an unpleasant odor as well as to the escape of its smelly contents, the fastening system is also used—as already indicated at the beginning—to secure the hygienic article in the rolled up or folded state. In the course of this, the first fastening section is pressed in a known manner on the outside of the rolled up or folded little package in such a way that it adheres, sticks, or is hooked there and prevents the unrolling or unfolding of the hygienic article.

The first fastening section at the rear of known hygienic articles is customarily provided on a section of the rear area, which is laterally widened in the shape of an hourglass, a so-called lateral flap, or on a fastening tongue which protrudes transversely with respect to the longitudinal direction, i.e. toward the sides, and which is fastened on the rear area, or respectively on the lateral flaps of the rear area. The second fastening section on the front area is either not clearly defined or is constituted by a surface which per se has mechanically acting securing means, or it extends mainly in the shape of a strip-shaped, transversely extending area at a band end section in the front area of the article. Therefore the first fastening section can be positioned, more or less overlapping the front area, in accordance with the body shape of the user.

Numerous solutions are known for designing the fastening system. For example, in European Patent 321 232 B1 it is suggested to embody the first fastening section in the shape of a tongue on the rear area in such a way that, besides a first partial section having the mechanically acting securing means, a second partial section is provided, which is provided with an application of an adhesive. Here, the first partial section with the mechanically acting securing means is used for closing the hygienic article when it is placed on the user in that the mechanical securing elements cooperate in the manner of a burr closure with mechanically acting counter-securing elements. The adhesive application in the second partial section is used for adhesively fastening the tongue on the layer of the article constituting the outside facing away from the body. When the used article is rolled together from the front area to the rear area, or is folded in such a way that the second fastening section lies in the interior of the little package, the little package is intended to be secured because of the cooperation of the adhesive second partial section with the foil-like, smooth exterior surface of the article. However, this fastening system has been shown to be disadvantageous in that the first fastening section, i.e. the fastening tongues, must be designed to be very large, or respectively long, corresponding to the two partial sections. The material requirements are therefore correspondingly large, and the laterally protruding tongues interfere with the handling of the article and appear unattractive. No defined holding power of the fastening system can be achieved, since in the course of closing there is a more or less extensive overlap or contact between the adhesively embodied second partial section and the vicinity of the second fastening section at the front, and a corresponding more or less strong adhesive connection, besides the intended mechanical connection of the securing means and counter-securing means. This indefiniteness must be considered to be disadvantageous.

Another approach for solving this problem is disclosed European Patent EP 0 321 234 A1, in that a contact section with mechanically acting counter-securing means is separately provided on the layer constituting the outside facing away from the body, which cooperates in the rolled-up or folded configuration of the article with the first fastening section. No adhesive application is provided here. The arrangement of this further mechanically acting contact strip on the outside of the article is expensive, and handling in the process of folding the article is difficult and requires alertness, since the fastening section must be exactly positioned with respect to each other. But experience has shown that in this situation in particular it is difficult to provide this alertness since, in caring for small children, often only one hand is available for folding the diaper while it is intended to place an unused hygienic article under the small child almost simultaneously.

For fastening an hygienic article in the form of a sanitary napkin on an item of clothing, it is known from European Patent EP 0 393 953 B1 a to also use an application of adhesive on the outside of the napkin, facing the item of clothing in use. So that the napkin can be secured on the textile material of the item of clothing without sliding, tapering projections are provided on the outside of the napkin having the adhesive layer, which are pushed into the textile material and in this way secure the napkin without sliding. Such an embodiment of the first fastening section of the hygienic article under discussion should, however, prove itself not suitable, since in this case a cooperation with a foil-like outside of the article facing away from the body would not be possible.

In Published International Application WO 96/25905 it a was proposed to provide the first fastening section, or respectively the mechanically acting hook-like securing means, and simultaneously also the second fastening section, with mechanically acting securing means, partially with an application of an adhesive. It is disclosed that, when connecting the rear part and the front part when the article is placed on the user, both connecting mechanisms, i.e. those securing mechanically or extending behind each other, on the one hand, and adhesively, on the other hand, are intended to work together in combination in order to form the desired fastening. In this case the force required for undoing the connection is divided into a shearing force projected on a plane, and a pull-off force acting vertically with respect to the plane, wherein the former is attributed to the mechanical connecting mechanism and the latter primarily to the adhesive connection. In accordance with the teaching of this publication the term "adhesive material" is understood to mean such materials which make an adhesive connection only with other adhesive materials. Because the first, as well as the second fastening section are additionally provided with such an adhesive material, it is intended to achieve a strong adhering force, which aids the mechanical connection. The problem of securing the used hygienic article in the rolled-up or folded configuration is not addressed in this publication.

SUMMARY OF THE INVENTION

The present invention has as in the object improving an hygienic article of the type described at the outset in such a way that, when placing the article on the body of a user, the correct fit of the article is achieved, as well as a secure connection of the front and rear areas, and that the used article can be secured in a configuration suitable for throwing it away in an easily manipulatable manner.

This object is achieved by present invention with an hygienic article having the characteristics mentioned at the outset in that a) the counter-securing means (90) of the second fastening section (64) are free of adhesive and form, for closing the hygienic article when placed on the body, a mechanical securing connection with a first peel-off force of more than 1 N/25 mm with the securing means of the first fastening section, and b) the securing means of the first fastening section are designed to be adhesive in such a way, and the front area of the layer constituting the outside is designed, at least in the vicinity of the second fastening section, to be smooth in such a way that the securing means of the first fastening section adhere there with a second peel-off force, which is less than the first peel-off force, and c) the securing means of the first fastening section are designed to be adhesive in such a way, and the layer constituting the outside is designed to be smooth in such a way at least in the center area, that the securing means of the first fastening section adhesively adhere there with a peel-off force of at least 0.1 N/25 mm, in order to secure the hygienic article in a rolled-up or folded configuration.

By means of the continuing development of hygienic products a shape is achieved which corresponds increasingly better to the shape of a body. Inter alia, the invention present is based on the recognition that with an optimal design in particular, a perfect fit of the hygienic product, and therefore dependable protection against leakage and a pleasant feel, free from binding, for the wearer, is provided only if the fastening system, i.e. the first and second fastening sections, are positioned and secured in a correct manner, which corresponds to the fashioning of the article. Thus, in accordance with the invention present the hygienic article is laid out in such a way that in the course of putting on the hygienic article, a user of the hygienic article, the parents or the caregivers, are forced to use the fastening system in this way, i.e. to align and position the fastening sections on the rear and front areas in such a way with each other that the fastening sections at least almost completely cover each other or overlap, in order to provide the required holding force. This is achieved by means of the characteristics of the invention present mentioned above. If the fastening system is used negligently, so that the first fastening section only slightly overlaps the second fastening section, or even comes to lie a position offset in with respect thereto, for example below a second fastening section designed as a strip-like band, because of the embodiment in accordance with the invention present of the fastening system the user will easily realize that with this positioning a sufficient fastening of the system is not achieved. He will release the first fastening section again from the just selected position and position it on the second fastening section, which can be easily identified with a little attention.

By means of the invention it has been further recognized that, with the use of the fastening system for securing the hygienic article in a configuration suitable for disposal, a peel-off force of at least 0.1 N/25 mm, preferably of 0.5 to 1 N/25 mm, is sufficient. A further advantage of the embodiment in accordance with the invention present results from the fact that for the purpose of this securing it is not necessary to provide additional, hard-to-operate contact means, but that the respective first fastening section is designed in such a way that it adheres to any arbitrary place on the outside of the center area, possibly also of the rear area, in the manner stated.

It is expressly pointed out that the nature of the layer constituting the outside can be the same over its entire surface. In this way the first fastening section adheres in the vicinity of the second fastening section with the same second peel-off force of at least 0.1 N/25 mm as on the remaining outside of the layer, in particular of the center area and the rear area.

The holding forces called peel-off forces above are defined and measured in the way described below. A 25 mm wide test strip made of a material constituting the first fastening section with its securing means is made available for testing. This test strip is applied with a pressure force of 2 kg, using a roller device, to the counter-surface to be tested. This is either the second fastening section or the layer constituting the outside of the product, which forms the vicinity of the second fastening section and preferably also the remaining outside of the product, for example the center section, to which the first fastening section is applied for disposing the rolled-up hygienic article in order to secure the rolled-up or folded configuration. In this case this counter-surface has been applied to a rigid support. The support is fastened in a tension testing device, and the test strip is clamped to one traction cheek, so that a pull-off angle of 150 results, which is slightly reduced by a few degrees during the pull-off The test strip, i.e. the first fastening section, is pulled off the counter-surface at a constant velocity while the holding force, called the peel-off force, is measured. The measured peel-off force is recorded as a function of the distance.

It is now possible in a particularly advantageous manner to embody the layer forming the outside of the article in any arbitrary manner, in particular with an essentially smooth foil-like surface, or with a fibrous surface, particularly looking like a textile. In the first case, the still remaining holding force which, in the area of the vicinity of the second fastening section is unsatisfactory, but in the center area is still sufficient for the purpose of disposal, is essentially determined by the adhesive adhering effects. If the layer constituting the outside of the hygienic article has a fibrous, textile-appearing surface, the influence of the adhesive effect is reduced and the one regarding the mechanical connection mechanism is moved into the forefront. In that case the outside of the article in the vicinity of the second fastening section is still designed to be so smooth in the front area, that the second peel-off force occurring there preferably lies considerably below the first peel-off force.

It is understood that the mechanically acting securing means of the first fastening section can be covered with an adhesive, either totally or partially. It is furthermore pointed out that the mechanically acting securing means can also be made of an adhesive material.

Preferred embodiments of the securing means, as well as the embodiment of the second fastening section with the counter-securing means and the layer of the hygienic article forming the outside facing away from the body, ensue from the following.

It has been shown to be particularly advantageous if the securing means are constituted by protrusions with end areas capable of engaging from behind or being engaged from behind and having a geometry, or respectively dimensions, as recited hereinafter. The second fastening section is a fluff-like fibrous strip material extending along the band section of the front area. This can be a textile material, for example a woven or knit material wherein, however, nonwoven materials on a nonwoven fabric basis are preferably used. As a rule, such a uff-like material made on a nonwoven fabric basis has a two-layered structure with a support layer which, for example, can consist of a foil, a spunbonded material or a melt-blown nonwoven fabric, or the like, and a loop layer forming the counter-securing means, for example a card web or a spunbonded material, which is engaged by the securing means of the first fastening section, which can get hooked there.

The fluff-like material can furthermore have a print image which can be applied either to the support layer, or directly on the loop layer, or to a third, particularly a foil-like layer, which is then preferably positioned between the support layer and the loop layer.

It was found that the embodiment of the fluff-like fibrous material is of particular importance for the holding strength between the first fastening section of the rear area and the fluff-like material of the front area. The fiber thickness, fiber length, the mass per unit area of the fluff-like fibrous material are preferably provided in accordance with the following description.

It has been shown to be particularly advantageous if the fluff-like, fibrous material has raised places having the dimensions in accordance with the following description which form loops arranged in a regular pattern. The raised places forming the loops can be obtained in an advantageous manner by heat-sealing the fluff-like fibrous material against the support layer. It is possible to obtain a flat material compound made of a foil-like support layer and a fluff-like fiber layer from 3M Deutschland GmbH, Neuss, Germany, which has a parallel endless wave pattern of raised places made by the application of heat-sealing stampings extending parallel with respect to each other. A flat material compound with lozenge-shaped heat-sealing stampings can be obtained from Corovin GmbH, Peine, Germany.

The layer forming the outside facing away from the body, which can have a smooth surface, or at least a surface conveying a certain textile-like, fibrous character, is a foil, or preferably an at least two-layered, in particular three-layered nonwoven fabric-foil laminate. The three-layered laminate preferably comprises a foil-like melt-blown layer forming the outside, and a spunbonded layer adjoining it, and an inside located foil layer (spunbonded-melt-blown laminate).

Further characteristics, details and advantages of the present invention ensue from the attached claims, as well from as from the drawings and the subsequent description of a preferred embodiment of the hygienic product in accordance with the present invention.

BRIEF DESCRIPTION OF THE DRAWINGS

FIG. 1 is a plan view of an hygienic article in accordance with the present invention in the form of a diaper, FIG. 2 is a sectional view along the section plane II—II in FIG. 1.

DESCRIPTION OF THE PREFERRED EMBODIMENTS

Figure 3:
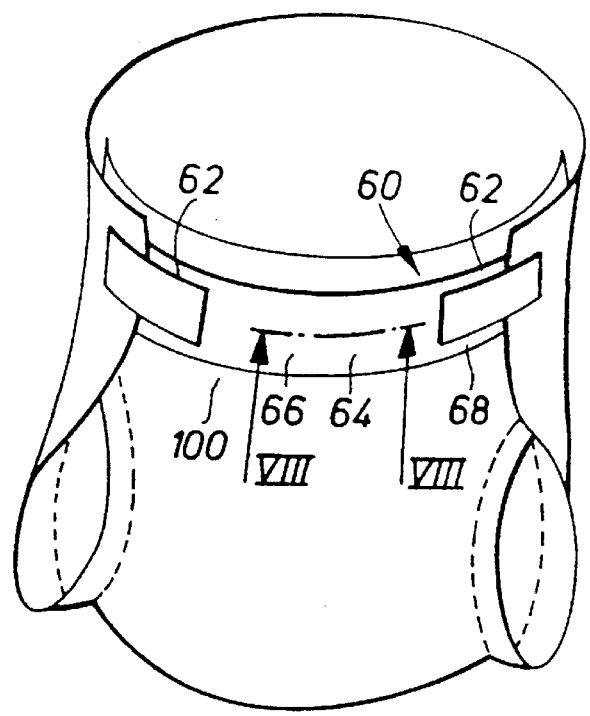
FIG. 3 is a perspective view of a diaper when applied to a user.

FIG. 1 represents an hygienic article in the form of a diaper 2 for a small child or for incontinent persons. The diaper 2 is arranged in the crotch area between the legs of a user and is then placed on the body upwardly in the direction toward the hips of the user and secured in a manner still to be described, so that a sort of pants is formed.

The diaper consists of a front area 4, a rear area 6 and a center area 8, located between them in the crotch area of the user of the diaper. The front area 4, the center area 8 and the rear area 6 are arranged in a longitudinal direction 10. The center area has two longitudinal edges 12 extending in the longitudinal direction 10, which extend curved toward the outside toward the front area 4 and the rear area 6 and make a transition into lateral flaps 14, 16 in the front area 4, and the rear area 6 respectively The longitudinal edges 18, 20 of the lateral flaps 14, 16 essentially again extend parallel with the longitudinal direction 10, but this is not necessarily required. Moreover, the front area 4 and the rear area 6 have a transverse edge 26, 28, which extends transversely with respect to the longitudinal direction 10 and borders a band end section 22, and 24, which respectively when the diaper 2 is worn, comes to lie in the hip area of the user. The respective longitudinal edge 12 of the diaper 2 with its course curving toward the outside in the direction toward the lateral flaps 14, 16, defines a respective leg opening when the diaper is worn.

An inner surface 30 forming the side of the diaper 2 facing the body is constituted by a liquid-permeable surface layer 32 extending in the longitudinal direction from the transverse edge 26 to the transverse edge 28. An absorbent body 34 is provided underneath the liquid-permeable surface layer 32 which—as can be seen in FIG. 1—has an hourglass-like circumferential shape and extends from one transverse edge 36 in the front area 4 as far as a transverse edge 38 in the rear area 6, wherein the transverse edges 36, 38 are located distance to the respective transverse edge 26, and 28, on respectively the order of centimeters. Thus, the absorbent body 34 is completely covered in the longitudinal direction by the upper, liquid-permeable surface layer 32. The surface layer 32 has two straight longitudinal edges 40, which are at such a distance from each other that in the center area 8 they extend past the absorbent body 34 transversely with respect to the longitudinal direction 10, while approximately in the area of the lateral flaps 14, 16, the hourglass-shaped absorbent body 34 projects from under the surface layer transversely with respect to the longitudinal direction 10 in the front area 4 as well as in the rear area 6.

A layer 44, which constitutes the outside 43 facing away from the body, of the diaper 2 is formed by a foil-like layer 46, which is impermeable to liquids, at least in a central longitudinal area 45, and borders the absorbent body 34 on the outside. To secure the extension and positioning of the absorbent body 34, the upper liquid-permeable layer 32 is connected with the outer layer 46, which is impermeable to liquids, along the transversely extending band end sections 22, 24 and along those sections of the longitudinal edges 40, which overlap the absorbent body 34 transversely with respect to the longitudinal direction 10, wherein per se arbitrary connections by means of an adhesive or by heat-sealing or the like can be used for this.

As can be furthermore seen in FIG. 1, first outer, and second inner elastic elements 48, respectively and 50, extend respectively at a distance from the longitudinal edges 12 and in the longitudinal direction 10 and form outer an inner, leg respectively closures. The outer and inner elastic elements are covered by a hydrophobic cover layer 52, which extends along the longitudinal edge 12 of the diaper from one transverse edge 26 to the other transverse edge 28. Transversely to the longitudinal direction 10, the cover layer 52 extends from the outside toward the inside as far as the inner elastic element 50 and forms a fold 54 there, which receives, or respectively encloses, the inner elastic element 50 in that an inner, longitudinally extending edge section 56 of the cover layer 52 is folded over and glued to the underside of the cover layer 52. In this way a small band 58, which rises in the direction toward the body surface of a user, is formed in the center area 8 of the diaper 2 by means of prestressing the inner elastic element 50. This small band 58 provided in the area of both leg closures extends as far as into the front area 4 and into the rear area 6 in order to be glued to, in particular sealed against, the inner surface 30 of the liquid-permeable surface layer 32 in the longitudinal direction 10 on the level of the lateral flaps 14, 16, in that the inner side of the fold 54, or respectively of the small band 58 is turned down. The inner elastic element 50 terminates in the longitudinal direction at a distance from the transverse edges 26, 28 of the diaper 2, and is also fastened in the area of the turned down and secured in place fold 54 in order to be able to exert a tension in the longitudinal direction, so that the small bands 58 "rise up". The outer elastic elements 48 have been glued, in particular sealed, while under longitudinal tension, between the cover layer 52 and the outer, foil-Eke layer 46, which is impermeable to liquids. They also terminate in the longitudinal direction 10 at a distance from the transverse edges 26, 28 which, however, is not necessarily required, but provides a tension-free band end section 22, and respectively 24.

A fastening system, identified as a whole by 60 (FIG. 3) is provided for closing the diaper when it has been put on the user. The fastening system 60 comprises a first fastening section 62 on both sides of the rear area 6, and a second fastening section 64, which constitutes a sort of a target area for the first fastening section 62 and is attached in the form of a band-shaped strip 66, still to be described in detail, on the outside of the front area 4.

The respective fastening section 62 is constituted by a band-shaped tongue 68. The tongue 68 is embodied in an approximate Y-shape and, from the longitudinal edge 30 of the respective lateral flap 16, it extends over the top, or respectively underside of the diaper 2 and is glued in place there. In its state where it is flipped toward the outside (see FIG. 1), the tongue 68 has mechanically acting fastening means 72 on its side 70 facing the body (FIG. 4, which is a schematic sectional view of section of the tongue 68 having the securing means 72). The mechanically acting securing means 72 are provided with protrusions 74, which are T-shaped or mushroom-shaped in cross section and have areas 76 capable of engaging from behind or being engaged from behind. A single such protrusion 74 is represented enlarged in FIG. 5. Such a protrusion comprises a stem 78 originating on a base 77 of the tongue 68, and a head 80 constituting the free end. The mechanical securing means 72, or respectively protrusions 74, have an adhesive coating 84 in the form of an adhesive of a permanent holding strength (not represented in FIG. 5) on a portion of their surface 82, or on the entire surface 82. In place of an adhesive coating, the securing means 72, or respectively the protrusions 74 can also be made altogether of a material having permanently adhesive properties.

Figure 4:
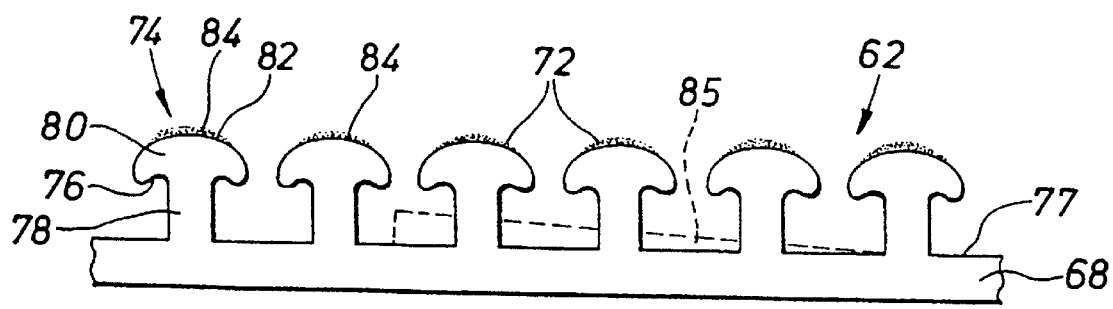
FIG. 4 is a schematic sectional view of a first fastening section of the diaper along the section plane IV—IV in FIG. 1.

It would also be conceivable for a further adhesive coating 85 to be provided on the base 77 in the area between the protrusions 74, by means of which the adhesive strength can be further increased when the tongue 68 is pressed with great force on an area on which the adhesive shows an adhesive effect. In this case it can be advantageous—as indicated in FIG. 4—if the thickness of the further adhesive coating is reduced transversely with in respect to the longitudinal direction 10, so that the free tongue end can be more easily freed when the tongue 68 is removed.

Figure 5:
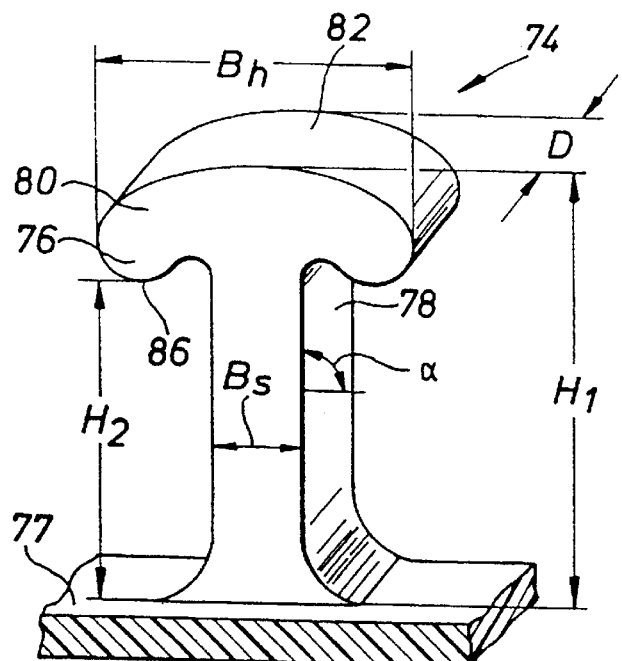
FIG. 5 is an enlarged representation of a mechanically acting securing means of the first fastening section in FIG. 4.

As can be seen from FIG. 5, the protrusions 74 have a total height H1 of 0.61 mm, wherein a distance H2 between a lower edge 86 of the area 76 which can be engaged from behind and the base 77 of the tongue 68 is 0.37 mm The thickness D of the stem 78 and the head 80 is 0.3 mm The width Bs of the stem is 0.21 mm in the represented case, and the width Bh of the head 80 is 0.55 mm The angle between the stem 78 and the base 77 is 90°. In accordance with a preferred embodiment, 87 protrusions per $cm^2$ of the base 77 of the tongue 68 are provided. It is pointed out that the above described form is a preferred embodiment, but that other embodiments of the protrusions are also possible.

Figure 6:
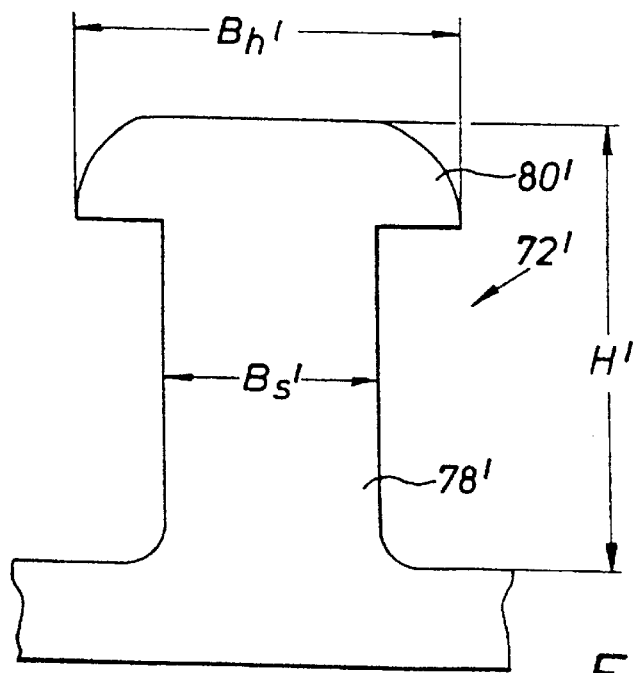
FIG. 6 is an enlarged representation of a second embodiment of a mechanically acting securing means.
Figure 7:
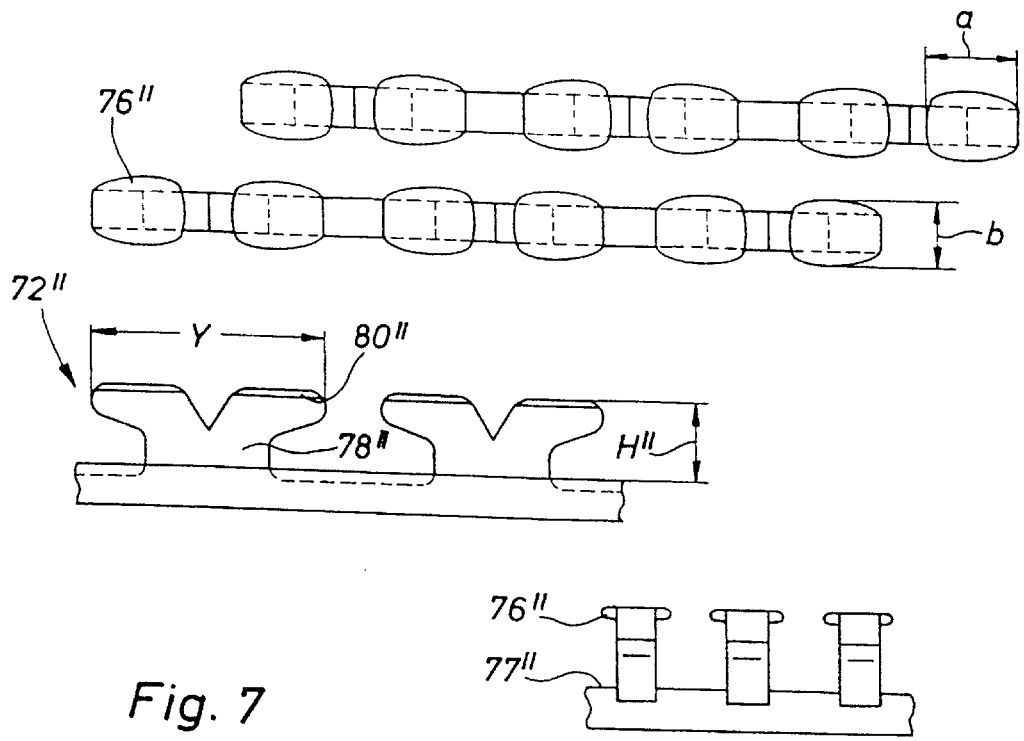
FIG. 7 is a representation of a third embodiment of a mechanically acting securing means.

FIG. 6 shows an embodiment of a mushroom-shaped securing means 72' with a circular cross section of the head and stem, whose head 80' has a width Bh' of 0.4 mm in comparison with a width Bs' of the stem 78' of 0.25 mm The height of the head H' in comparison with the base is 0.53 mm. FIG. 7 shows a third embodiment of securing means 72", which are Y-shaped in a plan view. The securing means 72" have a stem 78" of a thickness between 0.15 and 0.25 mm. The head 80" formed on the free leg forms a kind of a table surface for the adhesive to be applied. This table surface has a preferred dimension a, b of 0.27 times 0.25 to 0.35 mm The head 80" is embodied in such a way that it projects past the stem 78" in two directions, as illustrated in FIG. 7, and in this way forms an area 76" which can be engaged from behind. The height H" of the head above the base 77" is approximately 0.32 mm The length Y of both legs of the Y-shaped securing means 72" is 0.75 mm In this preferred embodiment, the flattening, as well as the course of the two free legs of the Y-shape, constitute an area which can be engaged from behind. At the same time the table-like flattening is particularly suited for an application of adhesive. The preferred distribution of the Y-shaped protrusions is approximately 250/cm$^2$.

Figure 8:
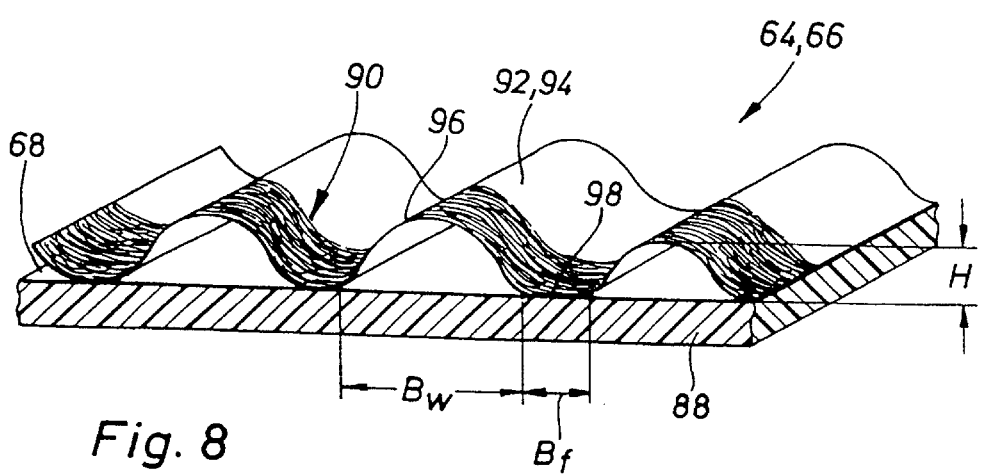
FIG. 8 is a sectional view of a second fastening section of the diaper along the section plane VIII—VIII in FIG. 1.

For closing the diaper 2, the first fastening section 62 mentioned in connection with FIG. 3 is pressed on the second fastening section 64, i.e. on the strip 66 in the front area 4. FIG. 8 shows a sectional view of the strip 66. It has a two-layered structure with a support layer 88 and a loop layer 92 of a fluff-like fibrous material 94, which constitutes the counter securing layer 90. The carrier layer can preferably be a foil, a spunbonded material or a melt-blown nonwoven fabric. In an advantageous manner, the loop layer 92 can be constituted by a card web or a spunbonded material, which can be engaged by the securing means 72 of the first fastening section 62, which can be hooked there. To this end the loop layer 92 has loop-forming raised places 96 which have been produced in that the nonwoven material, which preferably forms a nonwoven fabric 94, is secured in sections on the support layer 88 (reference numeral 98). Securing can take place along parallel lines—as represented in FIG. 8—or in the form of lozenge-shaped, triangularly-shaped or circular-shaped patterns by means of a heat-sealing process.

The design of the loop layer 92 is of great importance for the adhesive force. In the exemplary embodiment represented in FIG. 8, the raised places 96 form endless waves, wherein their width Bw is 2 to 5 mm, and the width of the secured surface 98 transversely with respect to its extension Bf is 0.2 to 5 mm. The height H of the raised places 96 preferably is 0.2 to 5 mm. A fiber thickness of the fluff-like material 94 of 6 to 9 dtex and a fiber length of 4 to 5 cm is preferably selected. The mass per unit area of the material 92 is 40 to 70 g/m$^2$. When, for closing the diaper, the tongue 68 is positioned in a correct manner on the strip 66 and is lightly pressed against it, the protrusions 74 enter into the loop layer 92 and are mechanically hooked therein, wherein a peel-off force of 2 to 4 N/25 mm is preferably achieved in order to assure that the diaper does not become undone in an accidental way.

In order to force the user of the diaper to close the diaper in the correct way, i.e. to position the first fastening section 62 in a correct manner on the second fastening section 64, so that an optimal fit of the diaper can be achieved, the vicinity 100 of the second fastening section 64, or respectively of the strip 66, is designed in such a away that, when the first fastening section 62 is positioned and pushed on it, it has a second peel-off force which is less than the first peel-off force. In case of a foil-like, very smooth outside 42, this second peel-off force is determined by the adhesive coat 84. However, it is also possible to provide the layer 44, which constitutes the outside 42 of the diaper facing away from the body, with a defined textile character. However, in such a case it is necessary that the outside 42 be embodied smooth or smoothed in the vicinity 100 of the second fastening section 64 in such a way that a peel-off force of 2 N/25 mm, in particular of 1 N/25 mm, is not exceeded. If a user of the diaper does not position the first fastening section 62 correctly with respect to the second fastening section 64, but instead in the vicinity 100, he is immediately advised of his error by the very low holding force in the vicinity 100 of the second fastening section, so that he would pull the first fastening section 62 off and position it again, but this time in the correct way, in relation to the second fastening section 64.

Figure 9:
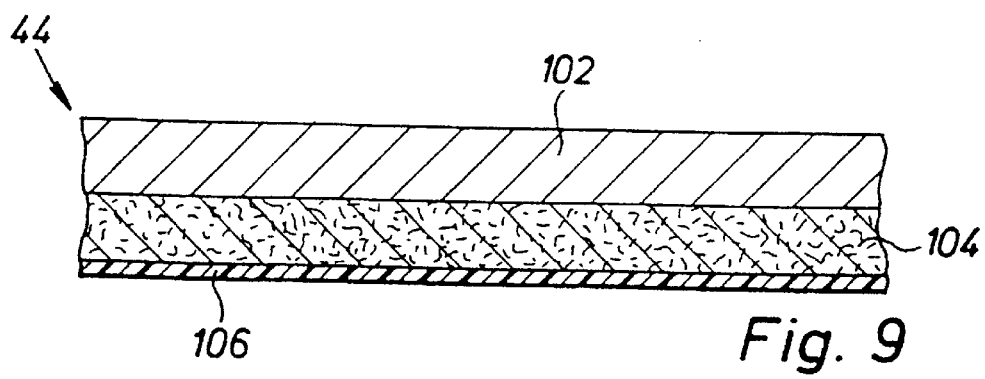
FIG. 9 is a sectional view through the layer constituting the outside of the diaper.

The layer constituting the outside 42 is embodied in the form of a spunbonded melt-blown laminate (FIG. 9), which comprises a foil-like melt-blown layer 102, an adjoining spunbonded nonwoven layer 104 and a foil layer 106 lying on the inside.

When the used diaper 2 is rolled up or folded for disposal, a user can press the first fastening section 62, or respectively tongues 68, anyplace on the outside—in the rolled-up state of the diaper the center area 6 would then present itself as an aiming point—so that the latter adhere on it at least with a peel-off force of at least 0.1, preferably of 0.5 to 1 N/25 mm This comparatively weak holding force has been shown to be sufficient for the purpose of securing the diaper in place in the rolled up or folded state and to toss it into a container in this state.

What is claimed is:

1. A hygienic article for one-time use, comprising:
   an outside layer facing away from the body of the user of the hygienic article, said outside layer being impermeable to liquid at least in a part thereof;
   an inside layer facing the body of the user of the hygienic article;
   an absorbent body situated between said outside layer and said inside layer, said inside layer being liquid permeable at least in the area of said absorbent body,
   said outside layer and said inside layer defining a front area, a rear area and a center area between said front area and said rear area, said center area lying in the crouch area of the user of the hygienic article; and
   a fastening system for the releasable connection of said rear area and said front area of the hygienic article when it is placed on the body of the user, and for securing the used article when it is rolled up or folded together for being thrown away or disposed of, said fastening system including a first fastening section with securing means at said rear area, and a second fastening section with counter-securing means at said front area, said first securing section being positioned on said second fastening section so that said securing means and said counter-securing means form a mechanical securing connection when said rear area and said front area are connected, wherein:
   said securing means includes an adhesive;
   said counter-securing means is free of adhesive, with said mechanical securing connection having a first peel-off force of more than 1 N/25 mm;
   said front area of said outside layer is smooth, at least in the vicinity of said second fastening section such that said securing means adheres there with a second peel-off force which is less than said first peel-off force; and said outside layer is smooth, at least in said center area, such that said securing means adhesively adheres there with a peel-off force of at least 0.1 N/25 mm, in order to secure the hygienic article in a rolled-up or folded configuration.

2. The hygienic article as defined in claim 1, wherein said first peel-off force is 2 to 4 N/25 mm.

3. The hygienic article as defined in claim 1, wherein said second peel-off force is 0.5 to 2 N/24 mm.

4. The hygienic article as defined in claim 1, wherein said second peel-off force is 0.5 to 1 N/25 mm.

5. The hygienic article as defined in claim 1, wherein said securing means comprises a base and one of hook-shaped; T-shaped; and mushroom-shaped projections, which can be engaged from behind and have a raised height of 0.2 to 1.5 mm vertically in relation to said base.

6. The hygienic article as defined in claim 5, wherein at their free ends said projections are shaped in such a way that they point back in the direction toward said base.

7. The hygienic article as defined in claim 5, wherein the distance between the free end of said projections and said base is 0.1 to 1.3 mm.

8. The hygienic article as defined in claim 5, wherein said projections have a stem and a head formed on said stem, and wherein the width of said stem is 0.1 to 0.4 mm and the width of said head is 0.2 to 0.8 mm.

9. The hygienic article as defined in claim 8, wherein the mutual thickness of said stem and head is 0.1 to 0.6 mm.

10. The hygienic article as defined in claim 8, wherein said stem extends at an angle of between 45° to 135° relative to said base.

11. The hygienic article as defined in claim 5, wherein said projections are 40 to 400 pieces per $cm^3$.

12. The hygienic article as defined in claim 5, wherein said projections are 50 to 100 pieces per $cm^3$.

13. The hygienic article as defined in claim 8, wherein the surface of said head is 0.05 to 0.5 mm.

14. The hygienic article as defined in claim 1, wherein said securing means comprise protrusions with a section engageable from behind, and wherein said protrusions have one of an X-shaped; and Y-shaped form, and flattened free ends.

15. The hygienic article as defined in claim 14, wherein said X-shaped and Y-shaped protrusions include a stem, and wherein said flattened free ends project in two opposite directions past its respective stem.

16. The hygienic article as defined in claim 15, wherein said flattened free ends have a dimension in each of said two opposite directions of 0.2 to 0.35 mm, and a vertical dimension of 0.2 to 0.4 mm.

17. The hygienic article as defined in claim 8, wherein, when viewed from above, the extension of said X-shaped and Y-shaped protrusions are 0.6 to 0.9 mm.

18. The hygienic article as defined in claim 14, wherein each X-shaped and Y-shaped protrusion has a stem, and wherein the thickness of said stem is 0.15 to 0.25 mm.

19. The hygienic article as defined in claim 14, wherein said section engageable from behind includes a head which is 0.1 to 0.3 mm thick.

20. The hygienic article as defined in claim 14, wherein said securing means further comprise a base and a free end of said protrusions, and wherein the distance of each of said free ends from said base is 0.25 to 0.4 mm.

21. The hygienic article as defined in claim 1, wherein said second fastening section comprises a fluff-like fibrous material comprising said counter-securing means.

22. The hygienic article as defined in claim 21, wherein said fluff-like fibrous material has a fiber thickness of 3 to 15 dtex.

23. The hygienic article as defined in claim 21, wherein said fluff-like fibrous material has a fiber thickness of 6 to 9 dtex.

24. The hygienic article as defined in claim 21, wherein said fluff-like fibrous material has a fiber length of 2 to 10 cm.

25. The hygienic article as defined in claim 21, wherein said fluff-like fibrous material has a fiber-length of 4 to 5 cm.

26. The hygienic article as defined in claim 21, wherein said fluff-like fibrous material has a mass per unit area of 15 to 120 $g/cm^2$.

27. The hygienic article as defined in claim 21, wherein said fluff-like fibrous material has a mass per unit area of 40 to 70 $g/cm^2$.

28. The hygienic article as defined in claim 21, wherein said fluff-like fibrous material include loop-forming raised places arranged in a regular pattern.

29. The hygienic article as defined in claim 28, wherein the thickness of said loop-forming raised places is 0.2 to 5 mm.

30. The hygienic article as defined in claim 28, wherein said loop-forming raised places are produced by one of heat-sealing; gluing; and welding of said fluff-like fibrous material, and wherein the width of said heat-sealing, said gluing and said welding is 0.1 to 10 mm.

31. The hygienic article as defined in claim 30, wherein the width of said heat-sealing, said gluing and said welding is 0.2 to 5 mm.

32. The hygienic article as defined in claim 28, wherein the width of said loop-forming raised places-is 1 to 10 mm.

33. The hygienic article as defined in claim 28, wherein the width of said loop-forming raised places is 2 to 5 mm.

34. The hygienic article as defined in claim 1, wherein said second fastening section includes a double-layered structure with a support layer and a loop layer, said loop layer comprising said counter-securing means, which are hooked by said securing means of said first fastening section.

35. The hygienic article as defined in claim 1, wherein said outside layer is a foil.

36. The hygienic article as defined in claim 1, wherein said outside layer is at least a two-layer nonwoven material-foil laminate.

37. The hygienic article as defined in claim 36, wherein said outside layer is a three-layer laminate comprising a melt-blown layer, forming the outside, an adjoining spunbound nonwoven layer and a foil layer forming the inside.

38. The hygienic article as defined in claim 37, wherein the mass per unit area of the spunbound nonwoven layer is 10 to 25 $g/m^2$.

39. The hygienic article as defined in claim 37, wherein the mass per unit area of the melt-blown layer is 3 to 15 $g/m^2$.

40. The hygienic article as defined in claim 37, wherein the thickness of the foil layer is 5 to 25 $\mu$m.

* * * * *